United States Patent [19]
Tozuka et al.

[11] Patent Number: 5,964,092
[45] Date of Patent: Oct. 12, 1999

[54] ELECTRONIC COOLING APPARATUS

[75] Inventors: Tadao Tozuka, Shizuoka; Kozo Suzuki, Tokyo, both of Japan

[73] Assignee: Nippon Sigmax, Co., Ltd., Japan

[21] Appl. No.: 08/937,558

[22] Filed: Sep. 25, 1997

[30]     Foreign Application Priority Data

Dec. 13, 1996  [JP]  Japan .................................. 8-333682

[51] Int. Cl.$^6$ ............................... A61F 7/10; H01L 35/34
[52] U.S. Cl. ................................................................ 62/3.7
[58] Field of Search ............................. 62/3.2, 3.3, 3.5, 62/3.7, 259.3

[56]              References Cited

U.S. PATENT DOCUMENTS

| | | | |
|---|---|---|---|
| 3,111,813 | 11/1963 | Blumentritt | 62/3.7 |
| 3,481,393 | 12/1969 | Chu et al. | 165/80 |
| 4,109,707 | 8/1978 | Wilson et al. | 165/46 |
| 4,829,771 | 5/1989 | Koslow et al. | 62/3.64 |
| 4,848,090 | 7/1989 | Peters | 62/3.3 |
| 4,930,317 | 6/1990 | Klein | 62/3.3 |
| 5,097,829 | 3/1992 | Quisenberry | 62/3.5 X |
| 5,154,661 | 10/1992 | Higgins et al. | 62/3.3 |
| 5,431,021 | 7/1995 | Gwilliam et al. | 62/3.7 |
| 5,561,981 | 10/1996 | Quisenberry et al. | 62/3.7 |
| 5,564,276 | 10/1996 | Abadilla et al. | 62/3.7 |
| 5,711,155 | 1/1998 | DeVilbiss et al. | 62/3.7 |
| 5,724,818 | 3/1998 | Iwata et al. | 62/3.7 |

FOREIGN PATENT DOCUMENTS

| | | | |
|---|---|---|---|
| 0 003 822 A1 | 9/1979 | European Pat. Off. | F28F 27/00 |
| 41 25 535 A1 | 2/1993 | Germany | F25B 21/04 |
| 57-22751 | 2/1982 | Japan . | |
| 4-77583 | 12/1992 | Japan . | |
| 8-84744 | 4/1996 | Japan . | |
| 868029 | 5/1961 | United Kingdom . | |
| 2 202 447 | 9/1988 | United Kingdom | A61F 7/00 |
| 2 286 660 | 8/1995 | United Kingdom | A61F 7/00 |
| WO 92/13243 | 8/1992 | WIPO . | |
| WO 94/00086 | 1/1994 | WIPO | A61F 7/00 |

OTHER PUBLICATIONS

Komatsu Electronics Products Guide (Apr. 1994).

*Primary Examiner*—William Doerrler
*Attorney, Agent, or Firm*—Rodney F. Brown

[57]              ABSTRACT

An electronic cooling apparatus which circulates a cooled refrigerant and supplies the refrigerant to a pad, includes a heat transfer path, 1st to nth electronic cooling devices, a temperature sensor, and a controller. The heat transfer path is arranged in a refrigerant supply path to the pad. The 1st to nth electronic cooling devices have cooling surfaces bonded to the heat transfer path such that heat can be transferred. The temperature sensor is attached to at least one of the cooling surfaces of the 1st to nth electronic cooling devices. The controller controls power supply to the 1st to nth electronic cooling devices on the basis of a temperature of the cooling surface of the electronic cooling device, which is detected by the temperature sensor, thereby maintaining a temperature of the refrigerant to the pad within a predetermined range.

26 Claims, 5 Drawing Sheets

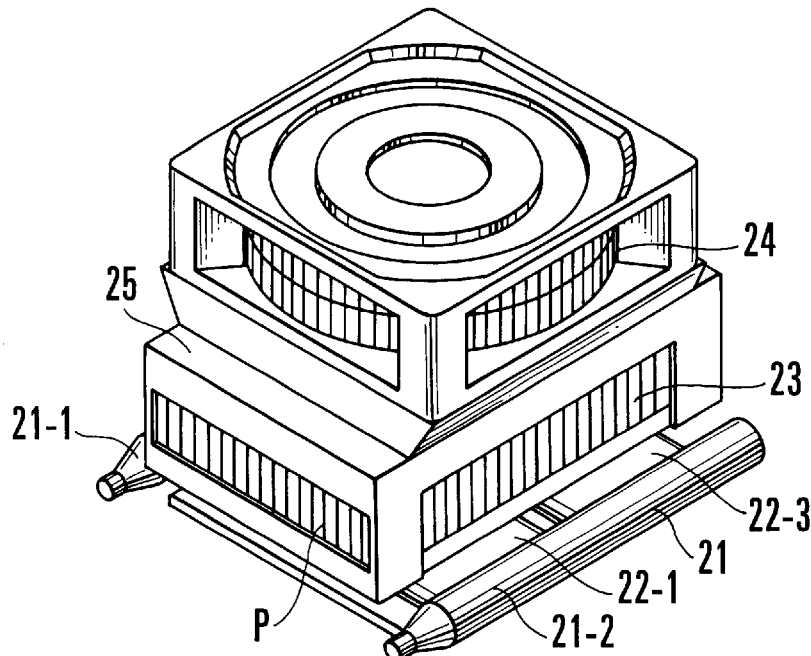
F I G. 2 A
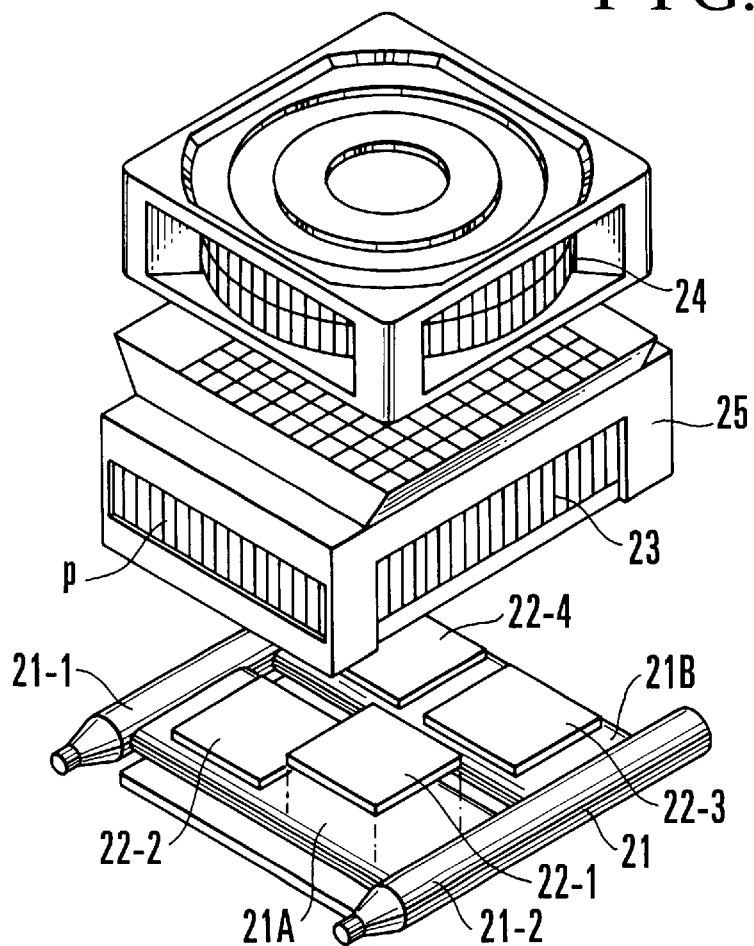
F I G. 2 B

ELECTRONIC COOLING APPARATUS

BACKGROUND OF THE INVENTION

The present invention relates to an electronic cooling apparatus which cools a refrigerant by an electronic cooling device using the Peltier effect, circulates the cooled refrigerant and supplies the refrigerant to a pad, thereby cooling the morbid portion of a patient, where the pad is applied.

As a conventional electronic cooling apparatus of this type, a therapeutic cooling apparatus is disclosed in Japanese Patent Publication No. 4-77583. FIG. 6 shows the basic arrangement of this therapeutic cooling apparatus. Referring to FIG. 6, reference numeral 1 denotes a cooling unit (pad) which is applied to the morbid portion of a patient; 2, a supply valve for controlling the flow rate of a refrigerant supplied to the inlet port of the cooling unit 1; 3, a refrigerant temperature adjustment means; 4, a pump for circulating the refrigerant; 5, an inlet-side measurement means, arranged between the supply valve 2 and the cooling unit 1, for measuring at least the temperature of the refrigerant; 6, an outlet-side measurement means, arranged downstream the outlet port of the cooling unit 1, for measuring at least the temperature of the refrigerant; and 7, a comparison means for comparing information obtained by the inlet-side measurement means 5 with that obtained by the outlet-side measurement means 6.

In this therapeutic cooling apparatus, the refrigerant is cooled by the temperature adjustment means 3, and the cooled refrigerant is circulated by the pump 4 and supplied to the cooling unit 1. A temperature $T_{in}$ of the refrigerant entering the cooling unit 1 is detected by the inlet-side measurement means 5 and supplied to the comparison means 7. The comparison means 7 controls the supply valve 2 on the basis of the difference between the detected temperatures $T_{in}$ and $T_{out}$, thereby adjusting the amount of refrigerant to be supplied to the cooling unit 1. At the same time, the comparison means 7 controls the temperature adjustment means 3, thereby maintaining the temperature $T_{in}$ of the refrigerant to the cooling unit 1 within a predetermined range.

In such a conventional therapeutic cooling apparatus, the temperature of the refrigerant to the cooling unit 1 is detected to control the temperature adjustment means 3. For this reason, temperature control is delayed, so no quick temperature control can be performed.

In addition, when the temperature of the refrigerant is directly detected by the inlet-side measurement means 5 and the outlet-side measurement means 6, these temperature detection units are arranged in a thin pipe, resulting in clogging.

SUMMARY OF THE INVENTION

The present invention has been made to solve the above problems, and has as its object to provide an electronic cooling apparatus which can perform quick temperature control, prevent clogging in a pipe, and detect an abnormality early.

In order to achieve the above object, according to the present invention, there is provided an electronic cooling apparatus which circulates a cooled refrigerant and supplies the refrigerant to a pad, comprising a heat transfer path arranged in a refrigerant supply path to the pad, 1st to nth electronic cooling devices having cooling surfaces bonded to the heat transfer path such that heat can be transferred, a temperature sensor attached to at least one of the cooling surfaces of the 1st to nth electronic cooling devices, and control means for controlling power supply to the 1st to nth electronic cooling devices on the basis of a temperature of the cooling surface of the electronic cooling device, which is detected by the temperature sensor, thereby maintaining a temperature of the refrigerant to the pad within a predetermined range.

BRIEF DESCRIPTION OF THE DRAWINGS

FIGS. 2A and 2B are perspective views showing the specific arrangement of a cooling unit in the electronic cooling apparatus;

DESCRIPTION OF THE PREFERRED EMBODIMENT

Figure 1:
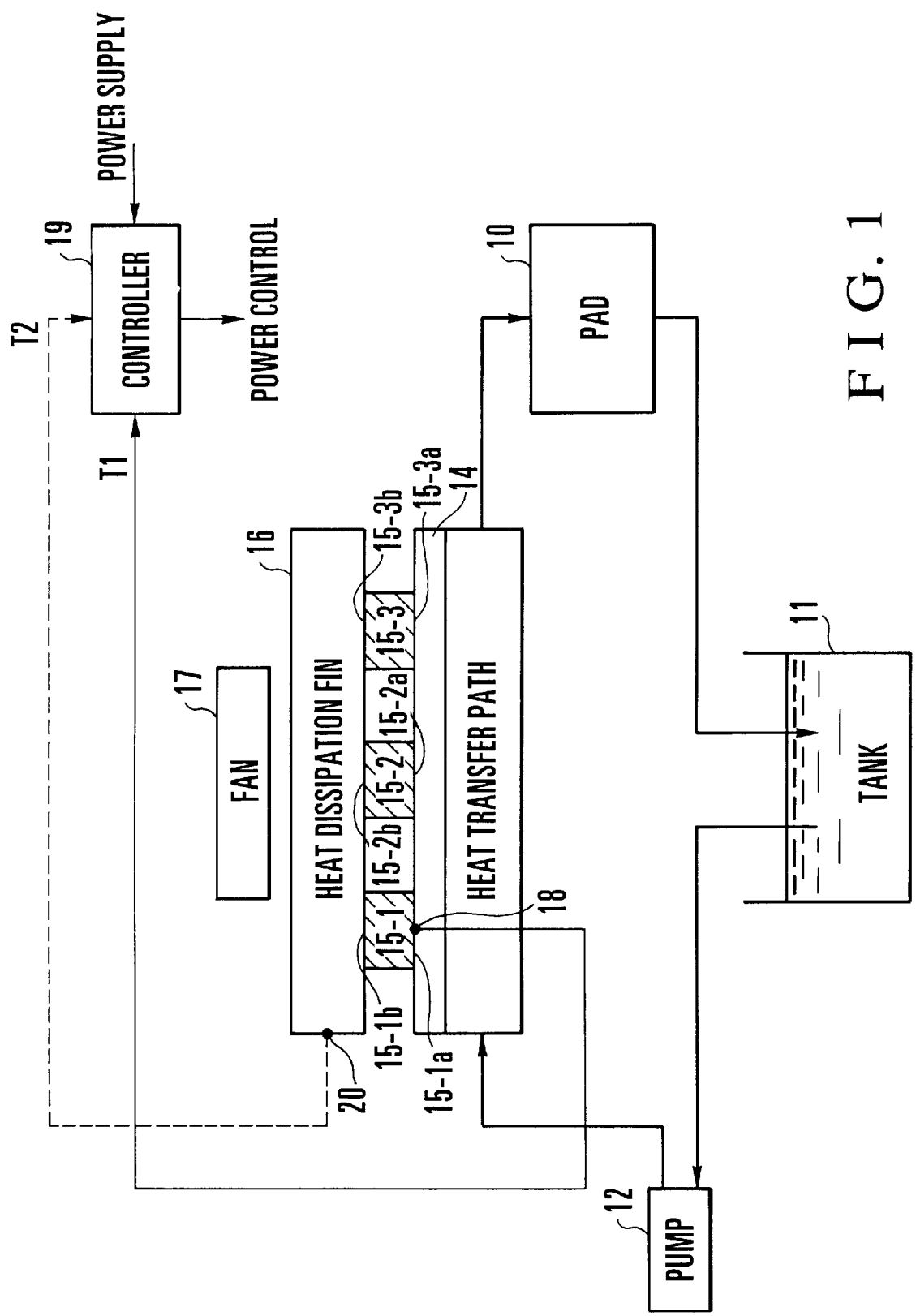
FIG. 1 is a view showing the basic arrangement of an electronic cooling apparatus according to an embodiment of the present invention.

An embodiment of the present invention will be described below in detail. FIG. 1 shows the basic arrangement of an electronic cooling apparatus according to the embodiment of the present invention.

Referring to FIG. 1, reference numeral 10 denotes a pad which is applied to the morbid portion of a patient; 11, a tank in which a refrigerant is stored; 12, a pump for circulating the refrigerant; 13, a heat transfer path arranged in a refrigerant supply path to the pad 10; 14, a heat insulating plate arranged on the upper surface of the heat transfer path 13; 15-1 to 15-3, electronic cooling devices whose cooling surfaces 15-1a to 15-3a are bonded to the heat transfer path 13 through the heat insulating plate 14 such that heat can be transferred; 16, a heat sink bonded to heat dissipation surfaces 15-1b to 15-3b of the electronic cooling devices 15-1 to 15-3 such that heat can be transferred; 17, a cooling fan; 18, a temperature sensor attached to the cooling surface 15-1a of the electronic cooling device 15-1, i.e., between the cooling surface 15-1a and the heat transfer path 13; and 19, a controller.

The pad 10 has refrigerant inlet and outlet ports and is formed of, e.g., a soft rubber or synthetic resin material. As the refrigerant, water such as pure water, or an aqueous magnesium chloride solution is used. The aqueous magnesium chloride solution allows the use of an electromagnetic flowmeter and also prevents freezing of water in the pad 10 even in case of a temperature drop to the freezing point. The heat transfer path 13 is constituted by a flat pipe. The heat insulating plate 14 has almost the same shape as that of the upper surface of the heat transfer path 13 and is in tight contact with the upper surface of the heat transfer path 13. The heat transfer path 13 and the heat insulating plate 14 are formed of aluminum. The heat transfer path 13 and the heat insulating plate 14 may consist of copper, a stainless steel, or titanium. The heat insulating plate 14 need not always be arranged.

The electronic cooling devices 15-1 to 15-3 use the Peltier effect. Each of these devices is constituted by bonding n- and p-type semiconductors. When a current is flowed, one junction face absorbs heat, and the other junction face generates heat. The surface for absorbing heat is a cooling surface, and that for generating heat is a heat dissipation surface.

The operation of this electronic cooling apparatus will be described below in conjunction with the function of the controller 19.

When the pump 12 is driven, the refrigerant stored in the tank 11 is supplied to the pad 10 through the heat transfer path 13 and then returned to the tank 11. During this circulation, the refrigerant supplied to the pad 10 is cooled by the electronic cooling devices 15-1 to 15-3 in the heat transfer path 13 arranged before the pad 10. More specifically, since the cooling surfaces 15-1a to 15-3a of the electronic cooling devices 15-1 to 15-3 are bonded to the heat transfer path 13 through the heat insulating plate 14 such that heat can be transferred, the heat transfer path 13 is uniformly cooled through the heat insulating plate 14 serving as a heat buffer, and the refrigerant passing through the heat transfer path 13 is cooled.

In this case, the controller 19 controls the power to be supplied to the electronic cooling devices 15-1 to 15-3 on the basis of a temperature T1 of the cooling surface 15-1a of the electronic cooling device 15-1, which is detected by the temperature sensor 18, thereby maintaining the temperature of the refrigerant to the pad 10 within a predetermined range. With the arrangement of this embodiment, quick temperature control can be performed. More specifically, the excess or deficiency of the cooling capability in the heat transfer path 13 immediately appears as an increase or decrease in temperature T1 of the cooling surface 15-1a of the electronic cooling device 15-1. Therefore, quick temperature control can be performed without any delay in adjustment of the cooling capability in the heat transfer path 13. In addition, according to this embodiment, since the refrigerant temperature need not be detected, no temperature detection unit need be arranged in the pipe, and clogging can be prevented. Furthermore, without arranging any temperature detection unit in the pipe, electrical leakage to the refrigerant in the pipe can be prevented, so that an electrical safety can be ensured.

The controller 19 detects an abnormality in the electronic cooling devices 15-1 to 15-3 on the basis of the temperature T1 of the cooling surface 15-1a of the electronic cooling device 15-1, which is detected by the temperature sensor 18. More specifically, if any one of the electronic cooling devices 15-1 to 15-3 has an abnormality, the temperature T1 of the cooling surface 15-1a of the electronic cooling device 15-1 falls outside the normal range. Hence, the controller 19 can detect the abnormality in the electronic cooling devices 15-1 to 15-3. If an abnormality is detected, the controller 19 performs a fail-safe operation according to the abnormal situation, e.g., stops power supply to the electronic cooling devices 15-1 to 15-3.

In this embodiment, an abnormality in the electronic cooling devices 15-1 to 15-3 is detected on the basis of the temperature T1 of the cooling surface 15-1a of the electronic cooling device 15-1, which is detected by the temperature sensor 18. However, when a temperature sensor 20 is attached to the heat sink 16, an abnormality in the electronic cooling devices 15-1 to 15-3 can be more clearly detected from a temperature T2 of the heat sink 16, which is detected by the temperature sensor 20. Alternatively, the temperature sensor 20 may be attached to the refrigerant supply path or the heat transfer path 13. With this arrangement as well, an abnormality in the electronic cooling devices 15-1 to 15-3 can be more clearly detected from the temperature T2 of the refrigerant supply path or the heat transfer path 13, which is detected by the temperature sensor 20.

In this embodiment, power supply to the electronic cooling devices 15-1 to 15-3 is controlled on the basis of the temperature T1 of the cooling surface 15-1a of the electronic cooling device 15-1. However, this control operation may be performed on the basis of the temperature of the heat dissipation surface 15-1b of the electronic cooling device 15-1 or the temperature difference between the cooling surface 15-1a and the heat dissipation surface 15-1b of the electronic cooling device 15-1. The temperature T2 of the heat sink 16 may also be used as a parameter for controlling the power to the electronic cooling devices 15-1 to 15-3. More specifically, the refrigerant temperature may be controlled on the basis of not only the temperature of the cooling surface 15-1a and the temperature of the heat dissipation surface 15-1b or the temperature difference between the heat dissipation surface 15-1b and the cooling surface 15-1a but also the temperature of the heat sink 16. In this case, as the power control technique, various control techniques are available: a technique of changing the waveform of a voltage or current, ON/OFF-control using pulses, or phase control using a triac or thyristor as well as a basic control technique of adjusting the voltage or current value.

In this embodiment, the three electronic cooling devices 15-1 to 15-3 are used. However, the number of electronic cooling devices is not limited to three, as a matter of course. In addition, the device to which the temperature sensor 18 is attached is not limited to the electronic cooling device 15-1. The temperature sensor 18 may be attached to the electronic cooling device 15-2 or 15-3. Furthermore, the temperature sensor 18 may be attached to the heat insulating plate 14.

Figure 3:
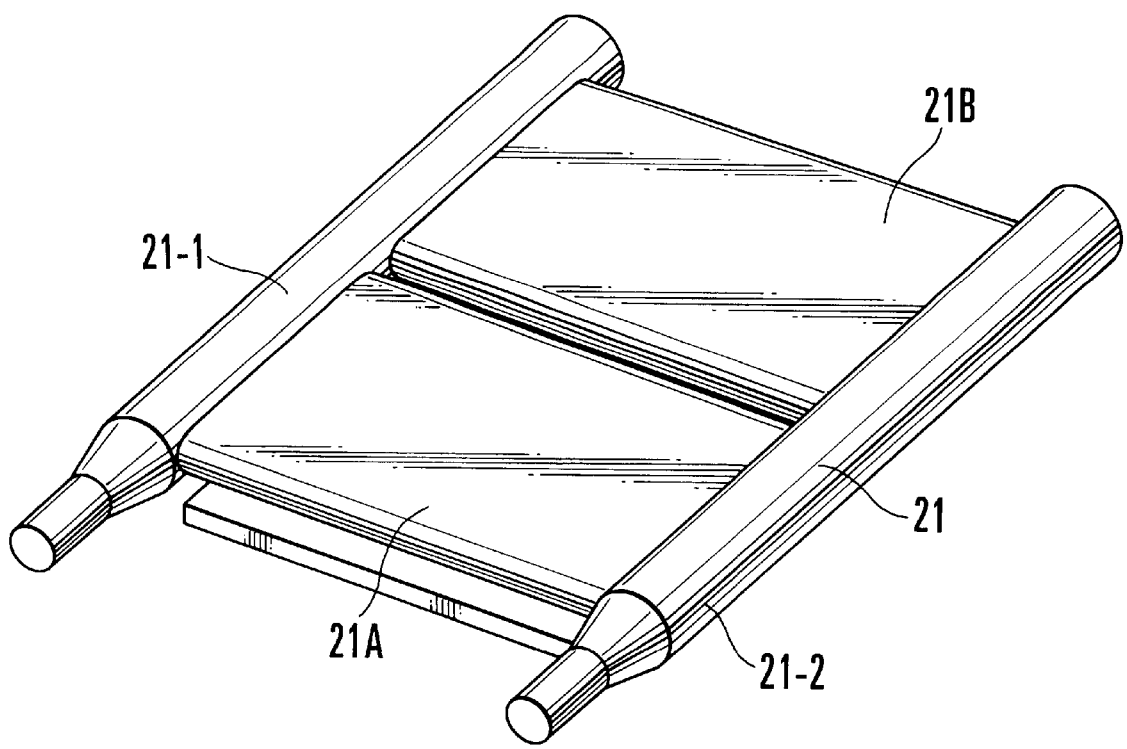
FIG. 3 is a perspective view showing a water-cooling jacket used in the cooling unit.

FIGS. 2A and 2B show the specific arrangement of the cooling unit in the electronic cooling apparatus. In this example, a water-cooling jacket 21 as shown in FIG. 3 is used as the heat transfer path. Peltier devices 22-1 to 22-4 are arranged on the upper surface of the water-cooling jacket 21. A heat sink 23 is arranged on the upper surfaces of the Peltier devices 22-1 to 22-4. A cooling fan 24 is arranged on the upper surface of the heat sink 23.

The water-cooling jacket 21 has a refrigerant inlet pipe 21-1, a refrigerant outlet pipe 21-2, and first and second main channels 21A and 21B each formed to communicate with a side portion of the inlet pipe 21-1 and a side portion of the outlet pipe 21-2. The Peltier devices 22-1 to 22-4 are arranged on the main channels 21A and 21B. The sectional area of each of the main channels 21A and 21B is larger than the sectional area of each of the inlet pipe 21-1 and the outlet pipe 21-2.

The heat absorbing capacity is proportional to a value obtained by integrating the flow rate per unit time by the passage time in the channel. For this reason, the heat exchange efficiency can be increased by reducing the flow velocity. More specifically, in this example, since the sectional area of each of the main channels 21A and 21B of the water-cooling jacket 21 is larger than the sectional area of each of the inlet pipe 21-1 and the outlet pipe 21-2, the flow velocity of the fluid passing through the main channels 21A and 21B is reduced, so that the heat exchange efficiency can be increased. In this example, the main channel has a two-forked shape. However, it is not limited to the two-forked shape, as a matter of course, and the main channel may be one.

Figure 4:
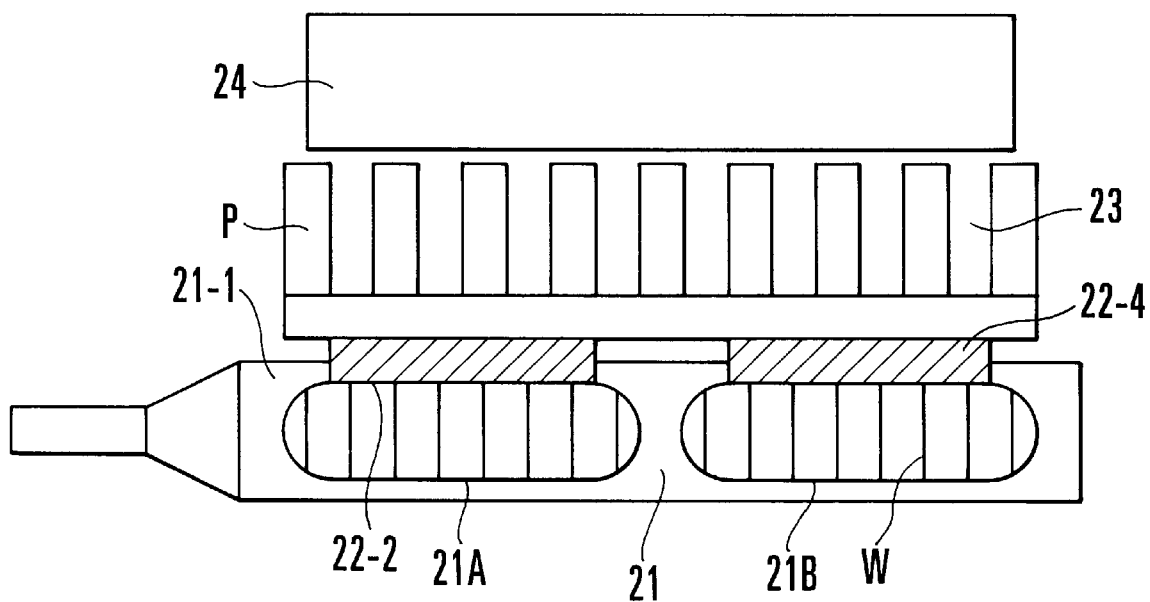
FIG. 4 is a side sectional view showing the cooling unit.

Each of the main channels 21A and 21B of the water-cooling jacket 21 has a number of ribs (partition walls) W arranged along the refrigerant flowing direction (FIG. 4). The heat absorbing capacity is proportional to the contact area of the heat absorbing surface. In this example, each of the main channels 21A and 21B is formed from a honeycomb member integrated with the ribs W. With this structure, the contact area between the inner wall of the water-cooling jacket 21 and the refrigerant increases to result in an increase in heat exchange efficiency.

Figure 5:
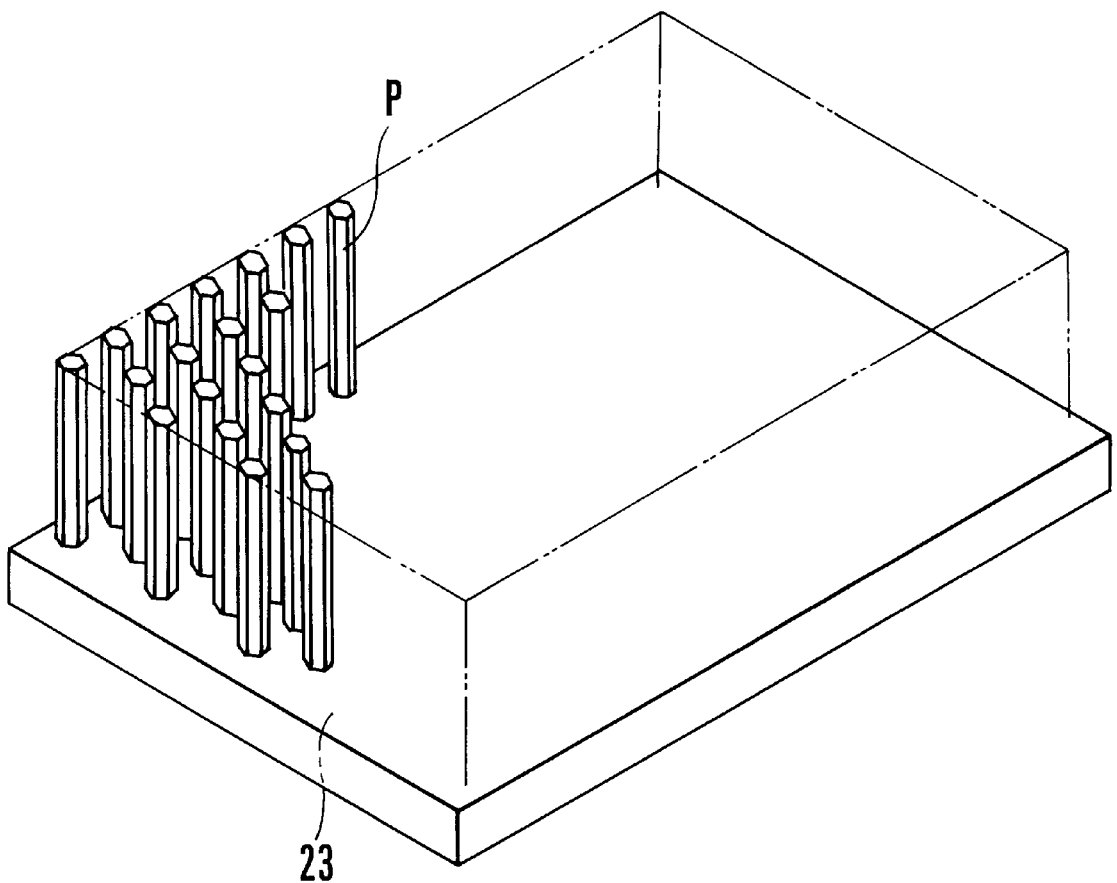
FIG. 5 is a perspective view showing a heat sink used in the cooling unit.
Figure 6:
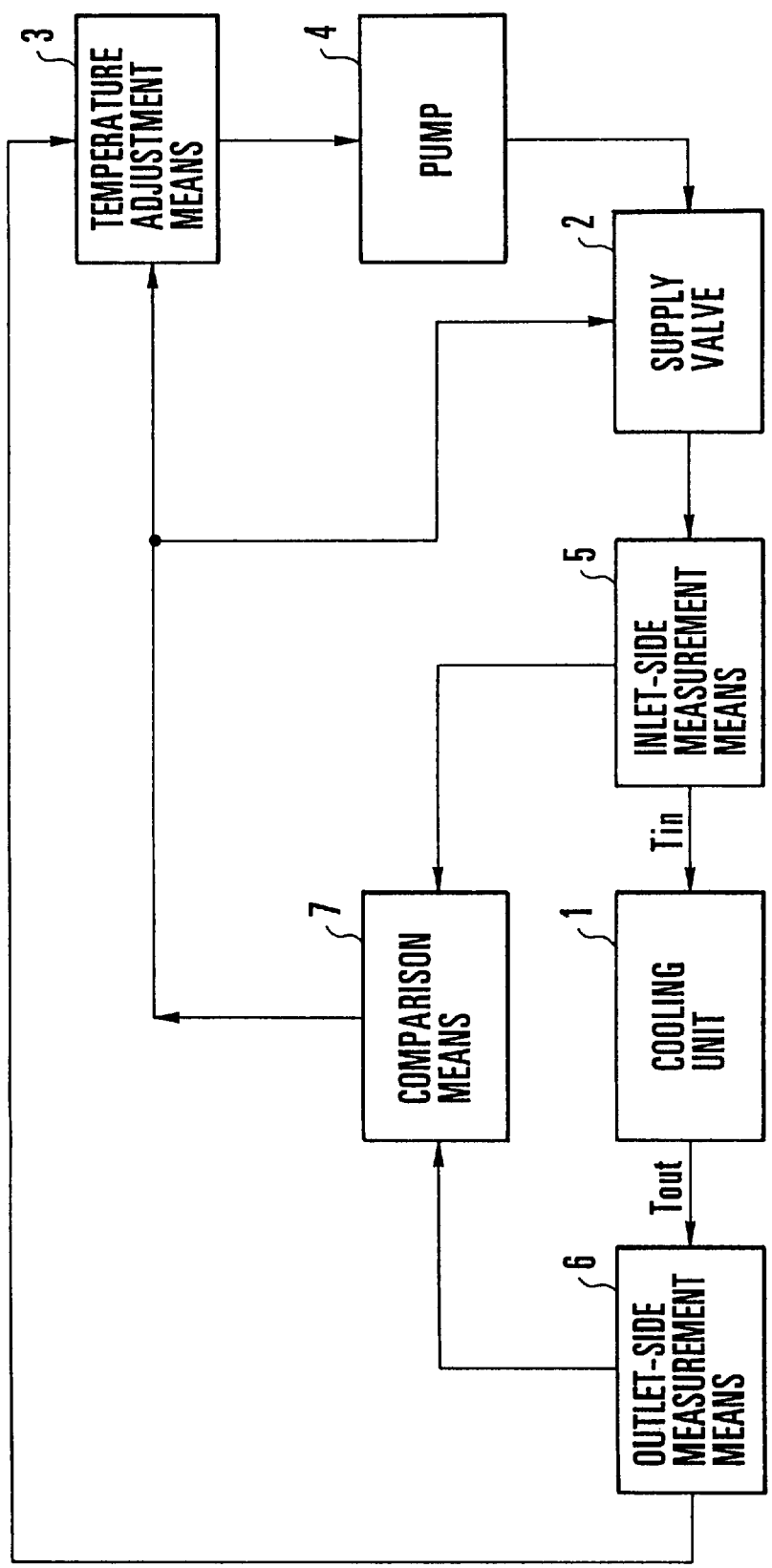
FIG. 6 is a block diagram showing the basic arrangement of a conventional therapeutic cooling apparatus.

The heat sink 23 is made of aluminum to absorb heat from the heat dissipation surface side of the Peltier devices 22-1 to 22-4. To increase the contact area with the outer atmosphere, i.e., to increase the heat dissipation area, the heat sink 23 has pins P each having a hexagonal prismatic shape (FIG. 5). In FIG. 2, a cover 25 is arranged to protect the heat sink 23 and simultaneously attach the cooling fan 24. A heat insulating member (not shown) is wound on the water-cooling jacket 21. The cooling fan 24 forcibly exhausts heat from the heat sink 23.

As has been described above, according to the present invention, power supply to the 1st to nth electronic cooling devices is controlled on the basis of the temperature of the cooling surface (the temperature of the heat dissipation surface, or the temperature difference between the cooling surface and the heat dissipation surface) of the electronic cooling device, so that the temperature of the refrigerant supplied to the pad is maintained within a predetermined range. The excess or deficiency of the cooling capability in the heat transfer path immediately appears as an increase or decrease in the temperature of the cooling surface (the temperature of the heat dissipation surface, or the temperature difference between the cooling surface and the heat dissipation surface) of the electronic cooling device. Therefore, quick temperature control can be performed without any delay in adjustment of the cooling capability in the heat transfer path.

In addition, according to the present invention, the honeycomb member integrated with the ribs to increase the sectional area of the channel and accordingly improve the heat absorbing capability, the heat sink having pins with a hexagonal prismatic shape to increase the heat dissipation area, and the cooling fan for forcibly cooling the air are used. With this arrangement, the heat exchange efficiency is increased to the maximum. For this reason, the cooling temperature necessary for temperature adjustment can be smoothly supplied, so that quicker temperature control can be performed.

Furthermore, according to the present invention, since the refrigerant temperature need not be detected, no temperature detection unit need be arranged in the pipe. With this arrangement, clogging can be prevented, and an abnormality can be detected early.

Furthermore, according to the present invention, the heat exchange efficiency can be increased to the maximum in accordance with the shape and arrangement of the heat transfer path or the heat sink. Therefore, the cooling output need not be wastefully increased, the power consumption is suppressed, and the entire apparatus can be made compact and lightweight.

What is claimed is:

1. An electronic cooling apparatus which circulates a cooled refrigerant and supplies the refrigerant to a pad, comprising:

a heat transfer path arranged in a refrigerant supply path to said pad;

1st to nth electronic cooling devices having cooling surfaces bonded to said heat transfer path such that heat can be transferred;

a temperature sensor attached to at least one of said cooling surfaces of said 1st to nth electronic cooling devices by positioning said temperature sensor between said cooling surface of said electronic cooling device and said heat transfer path bonded thereto; and control means for controlling power supply to said 1st to nth electronic cooling devices on the basis of a temperature of said cooling surface of said electronic cooling device, which is detected by said temperature sensor, thereby maintaining a temperature of said refrigerant to said pad within a predetermined range.

2. An electronic cooling apparatus which circulates a cooled refrigerant and supplies the refrigerant to a pad, comprising:

a heat transfer path arranged in a refrigerant supply path to said pad;

1st to nth electronic cooling devices having cooling surfaces bonded to said heat transfer path such that heat can be transferred;

a first temperature sensor attached to at least one of said cooling surfaces of said 1st to nth electronic cooling devices by positioning said temperature sensor between said cooling surface of said electronic cooling device and said heat transfer path bonded thereto:

a second temperature sensor attached to a heat sink contacting heat dissipation surfaces of said 1st to nth electronic cooling devices; and control means for controlling power supply to said 1st to nth electronic cooling devices on the basis of a difference between a temperature of said cooling surface of said electronic cooling device and a temperature of said heat sink, which is detected by said first and second temperature sensors, respectively, thereby maintaining a temperature of said refrigerant to said pad within a predetermined range.

3. An electronic cooling apparatus which circulates a cooled refrigerant and supplies the refrigerant to a pad, comprising:

a heat transfer path arranged in a refrigerant supply path to said pad;

1st to nth electronic cooling devices having cooling surfaces bonded to said heat transfer path such that heat can be transferred;

first and second temperature sensors respectively attached to at least one of said cooling surfaces and at least one of heat dissipation surfaces of said 1st to nth electronic cooling devices, wherein said first temperature sensor is attached to said cooling surface of said electronic cooling device by positioning said first temperature sensor between said cooling surface and said heat transfer path bonded thereto; and control means for controlling power supply to said 1st to nth electronic cooling devices on the basis of a difference between a temperature of said cooling surface and a temperature of said heat dissipation surface of said electronic cooling device, which are detected by said first and second temperature sensor, respectively, thereby maintaining a temperature of said refrigerant to said pad within a predetermined range.

4. An apparatus according to claim 1, further comprising a temperature sensor attached to a portion which is bonded to at least one of said heat dissipation surface and said cooling surface of each of said 1st to nth electronic cooling devices such that heat can be transferred.

5. An apparatus according to claim 1, further comprising a heat sink bonded to said heat dissipation surfaces of said 1st to nth electronic cooling devices such that heat can be transferred, and a temperature sensor attached to said heat sink, and wherein said control means controls power supply to said 1st to nth electronic cooling devices using, as one of parameters, a temperature of said heat sink, which is detected by said temperature sensor, thereby maintaining a temperature of said refrigerant to said pad within a predetermined range.

6. An apparatus according to claim 5, wherein said control means stops power supply to said 1st to nth electronic cooling devices when the temperature of said heat sink becomes not less than a predetermined value.

7. An apparatus according to claim 1, further comprising a heat sink having a number of prismatic pins and bonded to said heat dissipation surfaces of said 1st to nth electronic cooling devices such that heat can be transferred, and a cooling fan for exhausting heat from said heat sink.

8. An apparatus according to claim 1, wherein said heat transfer path has a refrigerant inlet pipe, a refrigerant outlet pipe, and a main channel communicating with said inlet pipe and said outlet pipe, said main channel having a sectional area larger than that of each of said inlet pipe and said outlet pipe.

9. An apparatus according to claim 1, wherein said heat transfer path has a refrigerant inlet pipe, a refrigerant outlet pipe, and first and second main channels each formed to communicate with a side portion of said inlet pipe and a side portion of said outlet pipe, each of said first and second main channels having a sectional area larger than that of each of said inlet pipe and said outlet pipe.

10. An apparatus according to claim 8, wherein said transfer path has, in said main channel, a number of partitions along a refrigerant flowing direction.

11. An apparatus according to claim 2, further comprising a temperature sensor attached to a portion which is bonded to at least one of said heat dissipation surface and said cooling surface of each of said 1st to nth electronic cooling devices such that heat can be transferred.

12. An apparatus according to claim 3, further comprising a temperature sensor attached to a portion which is bonded to at least one of said heat dissipation surface and said cooling surface of each of said 1st to nth electronic cooling devices such that heat can be transferred.

13. An apparatus according to claim 3, further comprising a heat sink bonded to said heat dissipation surfaces of said 1st to nth electronic cooling devices such that heat can be transferred, and a temperature sensor attached to said heat sink, and
wherein said control means controls power supply to said 1st to nth electronic cooling devices using, as one of parameters, a temperature of said heat sink, which is detected by said temperature sensor, thereby maintaining a temperature of said refrigerant to said pad within a predetermined range.

14. An apparatus according to claim 2, wherein said control means stops power supply to said 1st to nth electronic cooling devices when the temperature of said heat sink becomes not less than a predetermined value.

15. An apparatus according to claim 13, wherein said control means stops power supply to said 1st to nth electronic cooling devices when the temperature of said heat sink becomes not less than a predetermined value.

16. An apparatus according to claim 2, further comprising a heat sink having a number of prismatic pins and bonded to said heat dissipation surfaces of said 1st to nth electronic cooling devices such that heat can be transferred, and a cooling fan for exhausting heat from said heat sink.

17. An apparatus according to claim 3, further comprising a heat sink having a number of prismatic pins and bonded to said heat dissipation surfaces of said 1st to nth electronic cooling devices such that heat can be transferred, and a cooling fan for exhausting heat from said heat sink.

18. An apparatus according to claim 2, wherein said heat transfer path has a refrigerant inlet pipe, a refrigerant outlet pipe, and a main channel communicating with said inlet pipe and said outlet pipe, said main channel having a sectional area larger than that of each of said inlet pipe and said outlet pipe.

19. An apparatus according to claim 3, wherein said heat transfer path has a refrigerant inlet pipe, a refrigerant outlet pipe, and a main channel communicating with said inlet pipe and said outlet pipe, said main channel having a sectional area larger than that of each of said inlet pipe and said outlet pipe.

20. An apparatus according to claim 2, wherein said heat transfer path has a refrigerant inlet pipe, a refrigerant outlet pipe, and first and second main channels each formed to communicate with a side portion of said inlet pipe and a side portion of said outlet pipe, each of said first and second main channels having a sectional area larger than that of each of said inlet pipe and said outlet pipe.

21. An apparatus according to claim 3, wherein said heat transfer path has a refrigerant inlet pipe, a refrigerant outlet pipe, and first and second main channels each formed to communicate with a side portion of said inlet pipe and a side portion of said outlet pipe, each of said first and second main channels having a sectional area larger than that of each of said inlet pipe and said outlet pipe.

22. An apparatus according to claim 9, wherein said transfer path has, in said main channel, a number of partitions along a refrigerant flowing direction.

23. An apparatus according to claim 18, wherein said transfer path has, in said main channel, a number of partitions along a refrigerant flowing direction.

24. An apparatus according to claim 19, wherein said transfer path has, in said main channel, a number of partitions along a refrigerant flowing direction.

25. An apparatus according to claim 20, wherein said transfer path has, in said main channel, a number of partitions along a refrigerant flowing direction.

26. An apparatus according to claim 21, wherein said transfer path has, in said main channel, a number of partitions along a refrigerant flowing direction.

* * * * *